(12) United States Patent
de Wild et al.

(10) Patent No.: US 8,408,906 B2
(45) Date of Patent: Apr. 2, 2013

(54) DENTAL IMPLANT HAVING A SURFACE MADE OF A CERAMIC MATERIAL

(75) Inventors: Michael de Wild, Oberwil (CH); Frank Homann, Munich (DE)

(73) Assignee: Straumann Holding AG, Basel (CH)

( * ) Notice: Subject to any disclaimer, the term of this patent is extended or adjusted under 35 U.S.C. 154(b) by 145 days.

(21) Appl. No.: 12/105,700

(22) Filed: Apr. 18, 2008

(65) Prior Publication Data

US 2008/0261179 A1    Oct. 23, 2008

(30) Foreign Application Priority Data

Apr. 19, 2007  (EP) ..................................... 07007950

(51) Int. Cl.
*A61C 8/00*    (2006.01)
(52) U.S. Cl. ...................................... 433/201.1; 216/52
(58) Field of Classification Search .......... 433/172–176, 433/201.1; 428/141, 156, 172, 174, 409; 501/134, 152–154; 216/52, 74–77, 79, 96, 216/99–102
See application file for complete search history.

(56) References Cited

U.S. PATENT DOCUMENTS

| | | | |
|---|---|---|---|
| 6,165,925 A | 12/2000 | Rieger | |
| 6,174,167 B1 | 1/2001 | Wohrle | |
| 6,270,347 B1 | 8/2001 | Webster | |
| 6,933,025 B2 * | 8/2005 | Lin et al. ...................... | 428/34.6 |
| 2004/0265781 A1 * | 12/2004 | Coatoam ....................... | 433/173 |
| 2005/0064007 A1 | 3/2005 | Steinemann et al. | |
| 2005/0106534 A1 | 5/2005 | Gahlert | |
| 2006/0219661 A1 | 10/2006 | Towse et al. | |
| 2006/0246399 A1 | 11/2006 | Ehrl | |

FOREIGN PATENT DOCUMENTS

| | | |
|---|---|---|
| DE | 4012731 A | 10/1990 |
| DE | 19530981 | 2/1997 |
| DE | 10 2005 013200 | 9/2006 |
| EP | 0 388 576 | 9/1989 |
| EP | 0 870 478 A | 10/1998 |
| EP | 1529498 | 5/2005 |
| EP | 1450722 | 9/2005 |
| WO | WO 01/34056 A1 | 5/2001 |
| WO | WO 2005/027771 A1 | 3/2005 |
| WO | WO 2005/044134 | 5/2005 |
| WO | WO 2006/035011 | 4/2006 |

OTHER PUBLICATIONS

Smith et al. "An evaluation of the tribological performance of zirconia and CoCrMo femoral heads". Journal of Materials Science 34 (1999), pp. 5159-5162.*
Szmukler-Moncler et al. "Etched Implants: A Comparative Surface Analysis of Four Implant Systems". Journal of Biomedical Mater Res Part B: Appl Biomater 69B: 46-57, 2004.*
Lamolle et al. "Titanium implant surface and modifaction by cathodic reducting in hydrofluoric acid: Surface characterization and in vivo performance". Wiley InterScience. Feb. 27, 2008.*

(Continued)

*Primary Examiner* — Cris L Rodriguez
*Assistant Examiner* — Edward Moran
(74) *Attorney, Agent, or Firm* — Novak Druce Connolly Bove & Quigg LLP

(57) ABSTRACT

A dental implant having a surface made of a ceramic material. The dental implant is characterized in that the surface has a topography defined by a Core Roughness Depth $S_k$ of less than 1 μm.

19 Claims, 15 Drawing Sheets

OTHER PUBLICATIONS

Hong et al, "A Study on Osteoblast-like Cell Responses to Surface Modifed Titanium", J. Korean Acad Prosthodont, vol. 41, No. 3, 2003, pp. 300-319.*

Wennerberg et al, "Experimental study of turned and grit-blasted screw shaped implants with special emphasis on effects of blasting material and surface topography", Biomaterials, Volumn 17, No. 1, 1996, pp. 15-22.*

Li et al., "Biomechanical comparison of the sandblasted and acid-etched and the machined and acid-etched titanium surface for dental implants", J. Biomed, Mater. Res. 2002, 60(2), pp. 325-332.

EP Search Report dated Oct. 2, 2007 in corresponding EP 07007950.4-1265.

EP Search Report dated Sep. 10, 2007 in related EP 07007949.6-2318 (co-pending U.S. Appl. No. 12/105,595).

Takemoto M. et al., "Bone-bonding ability of a hydroxyapatite coated zirconia aluminum nanocomposite with a microporous surface," J. Biomed. Mater. Res., 2006, 78A, pp. 693-701.

Gudehus, H.T. Untersuchung des Einwachscerhalters von Zirkoniumdioxed—Implantation in die Kieferknochensbruktier Eine experimentelle Studie am Miniaturschwein, Ressertation Ludwig—Maximilians—Universtat, Munich.

DIN 4776, "Determination of surface roughness parameters $R_k$, $R_{pk}$, $M_{r1}$, $M_{r2}$, serving to describe the material component of the roughness profile", May 1990, (in German and English).

* cited by examiner

DENTAL IMPLANT HAVING A SURFACE MADE OF A CERAMIC MATERIAL

FIELD OF THE INVENTION

The present invention relates to a dental implant having a surface made of a ceramic material.

BACKGROUND

Dental implants which are inserted into the jawbone, for example for the attachment of artificial teeth, have been successfully used for more than a decade. The major part of the dental implants currently used consists of titanium, since titanium is biocompatible, has a sufficiently low elastic modulus and a relatively high strength.

Apart from its biocompatibility and its mechanical properties, the osteointegrative properties of a dental implant are of major importance. A good osteointegration means that the implant, after reaching a primary stability by screwing it into the bone, safely ossifies within a short healing time so that a permanent bond between implant and bone is guaranteed.

When using titanium as the implant material, osteointegrative properties can be reached by suitable treatment of the implant's surface. To this end, the titanium surface has conventionally been mechanically roughened by a subtractive removing process, e.g. sandblasting, grinding or etching. Alternatively, the surface has been subjected to additive processes, e.g. coating with a textured surface.

U.S. Pat. No. 6,174,167 discloses implants having a surface for bone-tissue apposition, said surface being obtained by machining, application of a textured surface or blasting with particles. It also discloses acid etching, applying growth factor, protein or other materials that promote, enhance and/or maintain bone-tissue growth and/or apposition. The implant is made from a biocompatible material, preferably from titanium or an alloy thereof.

DE-A-4012731 describes a process for producing an implant made of titanium employing spark erosive techniques in order to provide a desired roughness to the implant's surface.

Osteointegration has turned out to be particularly efficient if mechanical roughening of the implant's surface is combined with subsequent etching of the roughened surface, as is for example described in Li et al., J. Biomed. Mater. Res. 2002, 60 (2), pages 325-332.

Similarly, EP-A-0388576 describes the treatment of a titanium implant by a blasting process and subsequent etching with a reducing acid, such as HF, HCl or HCl with $H_2SO_4$.

Conventional titanium implants which are subjected to such a combined treatment safely ossify within a healing time of about 3 to 4 months after insertion into the bone, thereby providing a permanent bond between the dental implant and the bone.

From an aesthetic point of view, titanium implants have, however, the disadvantage that they are dark in color and therefore mismatch with the natural tooth color.

In contrast, the color of ceramic materials can be closely matched to the natural tooth color. Efforts have thus been made to provide dental implants of which at least the parts that are visible after insertion are made of a ceramic material.

WO-A-0134056 refers to a dental implant consisting of an insertion component which can be fitted in the jawbone and a support component which after implantation protrudes beyond the jawbone. The document discloses that at least the support component is made of zirconia ceramic.

DE-A-19530981 refers to a prefabricated implant supra construction using a tooth-colored zirconia ceramic attached to titanium implants.

Despite their advantageous properties with regard to the color, the use of ceramic materials for dental implants have been limited by their low fatigue stability and thereby by their tendency to crack.

WO-A-2005/027771 relates to a process for preparing a dental installation in which a dispersion is applied on a substrate having a first porosity, said dispersion forming upon sintering a ceramic layer with a second porosity.

EP-A-0870478 relates to a dental retention element having a core of a high-strength material such as zirconia, said core being coated with a ceramic material which can be chemically and/or mechanically processed.

The dental installation and the dental retention element described in WO-A-2005/027771 and EP-A-0870478, respectively, have the disadvantage that the ceramic coating is easily chipped off.

A ceramic material having a high mechanical strength is disclosed in U.S. Pat. Nos. 6,165,925, 6,165,925 relates to an yttrium-stabilized zirconium oxide (zirconia) in predominantly tetragonal form for the production of a sintered semi-finished article as a starting material for the manufacture of a prosthesis.

In order to achieve a sufficient mechanical stability, the zirconia ceramic disclosed in U.S. Pat. No. 6,165,925 must be highly dense. The surface of said highly dense zirconia ceramic is clean cut, extremely hard and has essentially no porosity. A dental implant made of such a zirconia ceramic is thus bio-inert and has only weak osteointegrative properties.

A similar problem is dealt with in Takemoto M. et al. (J. Biomed. Mater. Res., 2006, 78A, pages 693-701) reporting on the bone-bonding ability of a hydroxyapatite coated zirconia-alumina composite.

A further attempt to provide an osteointegrative ceramic dental implant is disclosed in EP-B-1450722 relating to a dental implant made of zirconia ceramic which after abrasive blasting is subjected to a treatment using phosphoric acid, sulphuric acid, hydrochloric acid or mixtures thereof.

However, the level of osteointegration of the zirconia implants according to EP-B-1450722 revealed by their removal torque values have been shown to be lower compared to the conventionally used titanium implants. Although after implantation an initial increase of the removal torque values of the zirconia implants could be measured, a decrease was observed after a certain period. Corresponding studies are discussed in Gudehus, H. T.; Untersuchung des Einwachsverhaltens von Zirkoniumdioxid-Implantaten in die Kieferknochenstruktur—Eine experimentelle Studie am Miniaturschwein, Dissertation Ludwig-Maximilians-Universität München.

SUMMARY OF THE INVENTION

The present invention provides a dental implant having a surface made of a ceramic material and being at the same time highly osteointegrative.

The surface has a topography defined by the Core Roughness Depth (also known as "Kernal Roughness Depth") $S_k$ of less than 1 μm. The Core Roughness Depth $S_k$ is a 3D specific value.

DETAILED DESCRIPTION

Although there is no standard for the characterization of a topography with 3D specific values, these values can be derived by a simple devolvement from the respective 2D specific values.

For two dimensions, an extra procedure for filtering with suppression of the depth of roughness leads to the roughness profile according to DIN 4776. The definitions therein can directly be transformed into three dimensions.

In particular, the Core Roughness Depth $S_k$ can, as the 2D specific Core Roughness Depth $R_k$, be derived from the so-called Material Ratio Curve (also known as "Abbott curve").

The Abbott curve represents the height distribution of the surface's material. It is a cumulative function of the material portion of the surface at a particular depth below the highest peak of the surface. In other words, the Abbott curve describes the increase of the material portion of the surface with increasing depth of the roughness profile. At the highest peak, the material portion is 0%, while at the deepest recess (or "valley") the material portion is 100%. The minimal secant slope, i.e. a defined line of best fit, separates the Abbott curve into the three following ranges:

a) the Core Roughness Depth $S_k$ [μm], i.e. the depth of the roughness core profile, b) the reduced Peak Height $S_{pk}$ [μm], i.e. the averaged height of the peaks sticking out of the core range, and c) the reduced Groove Depth $S_{vk}$ [μm], i.e. the averaged depth of the grooves sticking out of the core range.

Figure 1:
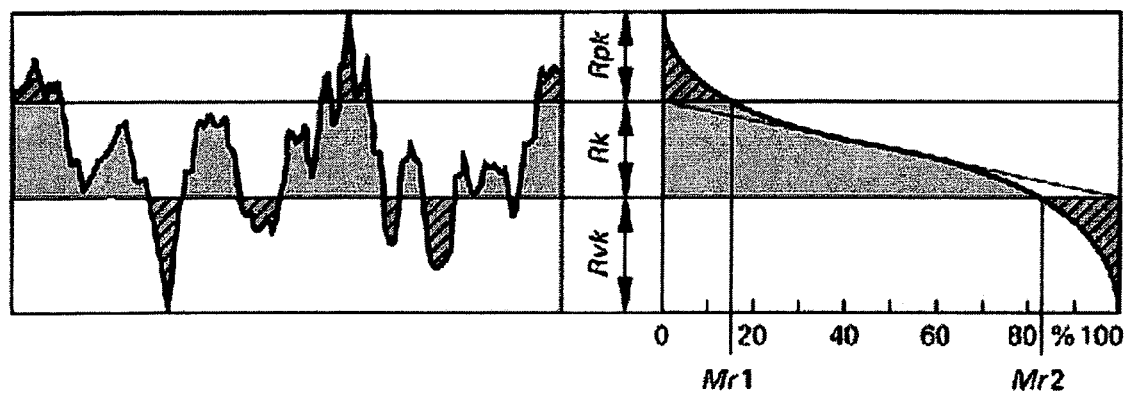
FIG. 1 is an idealized Abbott curve from which the 2D specific Core Roughness Depth $R_k$, the reduced Peak Height $R_{pk}$ and the reduced Groove Depth $R_{vk}$ are derived.

The concept how these values are derived from the Abbott curve are well known to the person skilled in the art. It is further illustrated in FIG. 1 showing an idealized Abbott curve from which the 2D specific Core Roughness Depth $R_k$, the reduced Peak Height $R_{pk}$ and the reduced Groove Depth $R_{vk}$ are derived. These parameters can directly be transformed to the 3D specific Core Roughness Depth $S_k$, reduced Peak Height $S_{pk}$ and reduced Groove Depth $S_{vk}$.

As shown in FIG. 1, the Core Roughness Depth $R_k$ or, in three dimensions, $S_k$ corresponds to the vertical distance between the left and right intercepts of the line through the ends of the minimal secant slope window of the Abbott curve. The location of the minimal secant slope window can be determined by shifting it along the Abbott curve until the slope between the two intersection points becomes minimal.

The topography can further be specified by the Skewness $S_{sk}$. The Skewness measures the symmetry of the variation of the surface about its mean plane. A Gaussian surface, having a symmetrical shape for the height distribution, has a Skewness of 0. A surface with a predominant plateau and deep recesses will tend to have a negative Skewness, whereas a surface having a number of peaks above average will tend to have a positive Skewness.

For a profile in two dimensions, the 2D specific Skewness $R_{sk}$ is according to DIN EN ISO 4287 defined by the following formula:

$$R_{sk} = \frac{1}{R_q^3} \cdot \frac{1}{N} \cdot \sum_{n=1}^{N} (z_n - \bar{z})^3$$

where $z_n$ is the height or depth of the respective peak or valley, respectively, $\bar{z}$ is the mean height and $R_q$ is the root-mean-square deviation of the surface.

For determining the Skewness $S_{sk}$ of the topography in three dimensions, the formula is transformed as follows:

$$S_{sk} = \frac{1}{S_q^3} \cdot \frac{1}{M \cdot N} \cdot \sum_{m=1}^{M} \sum_{n=1}^{N} (z_n - \bar{z})^3$$

where $S_q$ is the root-mean-square deviation of the surface according to the following formula:

$$S_q = \sqrt{\frac{1}{M \cdot N} \cdot \sum_{m=1}^{M} \sum_{n=1}^{N} (z_n - \bar{z})^2}$$

A detailed description how the $S_k$ and $S_{sk}$ values are determined in practice is given below under item 2 of the Examples.

Figure 2:
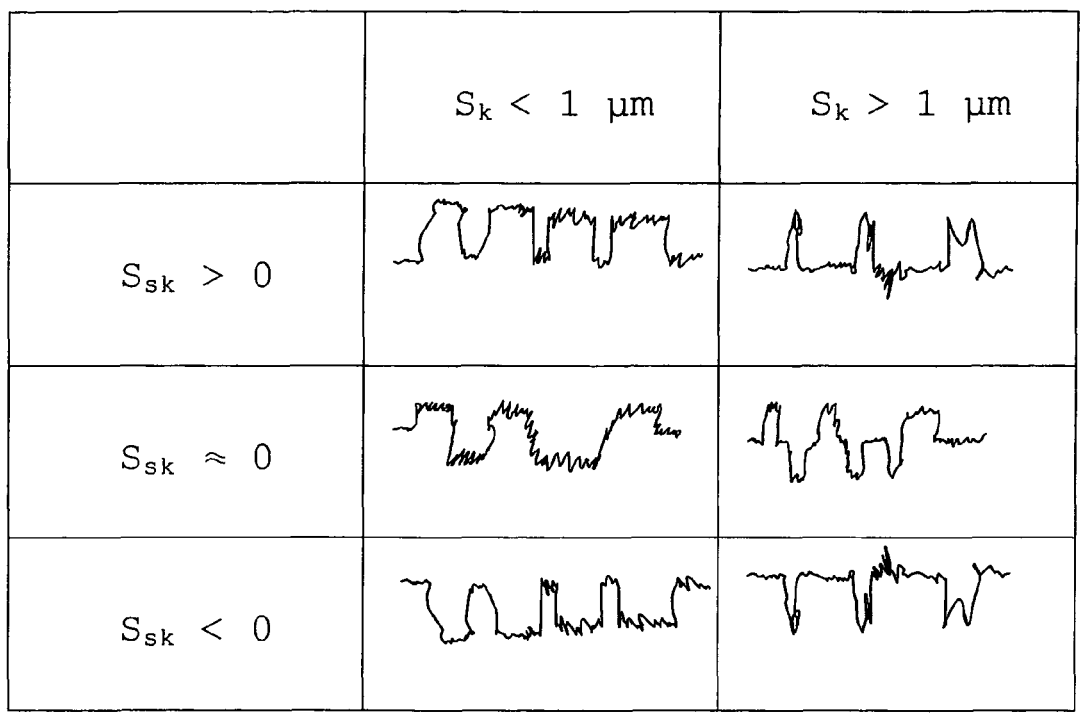
FIG. 2 is a graphical representation of different profiles defined by different $S_k$ and $S_{sk}$ values.

A graphical representation of different profiles defined by different $S_k$ and $S_{sk}$ values is given in the table shown in FIG. 2. In this table, the profiles shown in the first line have a positive Skewness $S_{sk}$, the profiles shown in the second line have a Skewness $S_{sk}$ of about 0 and the profiles shown in the third line have a negative Skewness $S_{sk}$. The profiles shown in the left column have a (low) Core Roughness Depth $S_k$ of less than 1 µm and the profiles shown in the right column have a (high) Core Roughness Depth $S_k$ of more than 1 µm.

According to the present invention, the topography has a Core Roughness Depth $S_k$ of less than 1 µm. Preferably, the Core Roughness Depth $S_k$ is between 0.3 µm and 1 µm, more preferably between 0.4 µm and 1 µm.

As can be seen from column 1 of FIG. 2, the main portion of such a topography is in the range of the extreme values; either the high peaks or the deep scratches are dominating over the core level. A dental implant having such a surface topography has been found to be highly osteointegrative.

The Skewness $S_{sk}$ of the topography of the present invention preferably falls within the following equation (I):

$$S_{sk} \leq -m^* S_k \qquad (I)$$

whereby m is from 0 to 1, preferably about 0.25, more preferably about 0.1.

More preferably, the Skewness $S_{sk}$ is less than 0, meaning that deep grooves in the topography are dominating.

It has been found that asymmetric topographies with deep grooves are highly osteointegrative, and that thereby the absolute roughness values ($S_a$, $R_{max}$, etc.) for example referred to in EP-B-1450722 are irrelevant.

The $S_k$ and $S_{sk}$ values of the topography of the present invention strongly differs from the topographies of commercially available implants, the osteointegrative properties of which have been studied in detail. It is thus highly surprising that the completely different topography of the dental implant of the present invention is osteointegrative.

The dental implant according to one embodiment of the present invention can be prepared by etching the surface made of a ceramic material by an etching solution comprising hydrofluoric acid at a temperature of at least 70° C., thereby removing discrete grains or agglomerates of grains from the ceramic material.

According to a preferred embodiment of the present invention, the ceramic material has an average grain size from about 0.1 µm to about 0.6 µm. Treatment of this material according to the etching described above leads to a surface topography with particularly high osteointegrative properties.

The term "ceramic material" encompasses any type of ceramic such as ceramics based on zirconia, alumina, silica or mixtures thereof, optionally comprising further constituents. Preferably, the ceramic material is based on zirconia, more preferably yttria-stabilized zirconia. Apart from the desired osteointegrative properties obtained, this material has the further advantage of a high fracture toughness and bending strength.

An example of an yttria-stabilized zirconia ceramic is described by the international standards ASTM F 1873 and ISO 13356, specifying the characteristics of, and a corresponding test method for, a biocompatible and biostable ceramic bone-substitute material based on yttria-stabilized tetragonal zirconia (yttria tetragonal zirconia polycrystals, Y-TZP) for use as material for surgical implants.

Specific examples of an yttria-stabilized zirconia are $ZrO_2$-TZP/TZP-A Bio-HIP® ($ZrO_2$) Bioceramic available from Metoxit AG, Switzerland, and ZIOLOX® available from CeramTec AG, Plochingen, Germany. Both materials offer a particularly high mechanical stability and strength, in particular when prepared by hot isostatic pressing or by sintering with subsequent hot isostatic densification. A detailed description of the $ZrO_2$-TZP/TZP-A Bio-HIP® ($ZrO_2$) Bioceramic is given in U.S. Pat. No. 6,165,925, the disclosure of which is incorporated herein by reference.

In particular, the composition of the yttria-stabilized zirconia comprises about 4.5 to about 5.5 weight-% of $Y_2O_3$ and less than about 5 weight-% of $HfO_2$, the total amount of $ZrO_2$, $Y_2O_3$ and $HfO_2$ being more than about 99.0 weight-%.

Coprecipitation is the most common method to distribute the yttria homogenously in the zirconia matrix. The stabilizing amount of yttria is added to the purified zirconium salt as an yttrium salt before the precipitation and calcination process is started, as described by Haberko K., Ciesla A., and Pron A., Ceramurgia Int.1 (1975) 111. Alternatively, the zirconia can be stabilized by yttria-coating. This initiates a radial gradient of yttria concentration in the powder, that is distributed in it kinetically during sintering, as described by Burger, W., Richter, H. G., Piconi, C., Vatteroni, R., Cittadini, A., Boccalari, M., New Y-TZP powders for medical grade zirconia. J Mater. Sci. Mater. Med. 1997, 8 (2), 113-118.

It is further preferred that prior to the etching described above a macroscopic roughness is provided to the ceramic surface of the dental implant by sandblasting, milling and/or injection molding techniques. Thus, a dental implant having especially good osteointegrative properties is obtained.

Sandblasting is generally performed using a pressure of 1 to 12 bar, preferably 4 to 10 bar. A considerably improved macroscopic roughness is achieved when using a hard material such as boron carbide. In a further preferred embodiment, $Al_2O_3$ particles having an average diameter of 250 to 500 µm are used.

As an alternative to sandblasting, the macroscopic roughness can also be provided by injection molding techniques. Injection molding techniques are known to a skilled person and are for example described in US-A-2004/0029075, the content of which is incorporated herein by reference. According to these techniques, casting molds with cavities are used, said cavities corresponding to the peaks of the molded implant's macroscopic roughness. The cavities of the casting mold are slightly greater in proportion than the peaks to be provided, taking into account the shrinking of the ceramic after injection molding. The casting molds themselves may be treated by sand blasting, anodization, laser and/or by erosion techniques in order to produce the cavities or the structured surface on the inner surface of the molds.

Injection molding techniques have the advantage that during this process no phase transformation occurs in the ceramic material which has therefore improved mechanical properties. Furthermore, the manufacture of the dental implant by injection molding circumvents the additional step of providing the macroscopic roughness and is thus quick. In addition, it has an excellent reproducibility and there is no contamination with particles from sandblasting.

It is also envisioned to provide a macroscopic roughness by milling or grinding. For this purpose, milling or grinding devices having a defined grain size are used in order to guarantee a desired macroscopic roughness of the surface.

For preparing the microstructure of the surface topography, it is further preferred that the etching solution described above comprises at least 50 vol.-%, more preferably at least 80 vol.-% of concentrated hydrofluoric acid. Etching with this etching solution leads after a relatively short etching time to a uniform topography over the whole surface treated.

The etching solution can further comprise at least one compound selected from the group consisting of phosphoric acid, nitric acid, ammonium fluoride, sulfuric acid, hydrogen peroxide and bromic acid. Preferably, the etching solution comprises sulfuric acid in an amount of 50 vol.-% at most.

The etching time depends highly on the etching solution used and typically ranges from about 10 seconds to about 120 minutes. The etching time is preferably about 1 minute to about 60 minutes, more preferably about 20 minutes to about 40 minutes and most preferably about 30 minutes.

Preferably, the etching is followed by washing the dental implant, the washing comprising the subsequent step or the subsequent steps of c) rinsing the dental implant with a NaCl solution and/or
d) rinsing the dental implant with deionized water.

The performance of the washing step can be improved by using ultrasound. Thereby, grains, grain agglomerates or reaction products which loosely adhere to the surface are effectively removed.

The dental implant may be for example a one-part or a two-part dental implant comprising an anchoring part for anchoring the implant within the jawbone and a mounting part for receiving a prosthetic build-up construction.

Two-part systems are known in the art. They can either be inserted subgingivally or transgingivally.

According to the (closed) subgingival system, the anchoring part of the dental implant is embedded until the bone ridge so that the mucoperiosteal cover can be seen above the implant. At the end of the primary healing phase, the mounting part and the desired bridge or crown is then applied in a second operation.

According to the (open) transgingival system, the anchoring part of the implant is sunk in up to about 3 mm of the bone ridge at mucosal level, thus avoiding a secondary operation. The wound edges can be directly adapted to the implant neck portion, thereby effecting a primary soft tissue closure to the implant. Then, the desired bridge or crown is screwed or cemented onto the mounting part of the implant, generally using an intermediate abutment.

Transgingivally applied dental implants are often preferred. When implanting such an implant, the soft tissue attachment during the healing process is not disturbed by a secondary operation such as occurring with systems that heal with covered mucous lining.

For example, the dental implant of the present invention can be a two-part, transgingivally applied implant analog to the titanium implant marketed by Institut Straumann AG, Basel/Switzerland, under the tradename "Straumann Dental Implant System".

The two-part dental implant preferably has an anchoring and a mounting part which are made of the same ceramic material. Thus, the anchoring part and the mounting part have the same thermal coefficient of expansion, allowing them to be closely fitted and avoiding the formation of gaps between them.

Alternatively, the dental implant of the present invention may also be a one-part dental implant. The mechanical stability of a one-part dental implant is generally higher than the one of a multi-part system. In combination with the high strength of the ceramic material used, the one-part dental implant of the present invention has thus a particularly high mechanical stability. The one-part dental implant has the additional advantage that there are no interstices and thus no starting points for the formation of bacteria which may cause parodontitis or gingivitis.

The dental implant of the present invention can be directly ground, allowing it to be adapted to further elements to be mounted in a simple way.

The dental implant of the present invention can either be made fully of a ceramic material or can have a core made of another material, such as a metal, for example titanium or an alloy thereof, or another ceramic material.

The present invention encompasses dental implants of which the whole surface is made of a ceramic material and dental implants of which only a part of the surface is made of a ceramic material.

Likewise, the present invention encompasses dental implants of which only a part of the surface has the topography according to the present invention. For example, the dental implant of the present invention may be an implant of which only the bone tissue contacting region of the anchorage part's surface has the topography according to the present invention. Likewise, only the region of the implant's surface contacting the soft tissue may have the topography according to the present invention. It has been found that when using a dental implant which in the soft tissue contacting region has the topography according to the present invention, the blood coagulum is stabilized which further accelerates the healing process. In a further embodiment of the present invention, both the bone and the soft tissue contacting region may thus have the topography according to the present invention.

It is further preferred that the anchoring part comprises a threaded section. Thereby, the implant can be implanted with the necessary primary stability so that directly subsequent to the implantation a primary treatment is made possible by applying a temporary measure. The surface of the threaded section preferably has the topography according to the present invention in order to increase osteointegration.

EXAMPLES

1. Etching of a Surface Made of Yttria-Stabilized Zirconia Ceramic

For Examples 1 to 11, densely sintered bodies made of yttria-stabilized zirconia ceramic as described by Burger, W. et al, New Y-TZP powders for medical grade zirconia. J Mater. Sci. Mater. Med. 1997, 8 (2), 113-118, and having the shape of a disc with a diameter of 15 mm and a thickness of 2 mm are prepared by low pressure injection molding and subsequent hot isostatic pressing. The material falls within the definition of ASTM F 1873 and ISO 13356 and is further specified by an average grain size from about 0.1 μm to about 0.3 μm.

For preparing the bodies, casting molds are used which optionally have been treated by erosion techniques to obtain a macroscopic roughness (or "macroroughness") on the inner surface of the mold. Depending on the erosion parameters used, a pronounced or a non-pronounced macroroughness is, thus, provided to the surface of the body. Alternatively, a pronounced macroroughness can also be obtained by sandblasting the bodies with $Al_2O_3$ at a pressure of 6 bar and an average working distance of 2 cm. Both the erosion and sandblasting techniques for providing a macroroughness to the surface are known to a person skilled in the art.

The bodies according to Examples 1 to 7 and 10 to 11 are then added to an etching solution in a Teflon container at a defined etching temperature and for a defined etching time. They are then instantly rinsed with deionized water and/or NaCl solution (200 mM) for five minutes in an ultrasonic device and subsequently dried under nitrogen or hot air.

Comparative Examples 8 and 9 are not added to the etching solution.

The particulars for Examples 1 to 11 are given in Table 1.

TABLE 1

| Example | etching solution | etching temperature | etching time | macroroughness |
|---|---|---|---|---|
| 1 | Mixture of 80 vol.-% HF and 20 vol.-% $H_2SO_4$ | 104° C. | 10 minutes | pronounced (erosion) |
| 2 | Concentrated HF | 104° C. | 10 minutes | pronounced (erosion) |
| 3 | Mixture of 85 vol.-% HF and 15 vol.-% $H_2SO_4$ | 102-104° C. | 5 minutes | non-pronounced |
| 4 | Mixture of 50 vol.-% HF and 50 vol.-% $H_2O$ | 102-104° C. | 5 minutes | non-pronounced |
| 5 | Concentrated HF | 102-104° C. | 10 minutes | non-pronounced |
| 6 | Mixture of 50 vol.-% HF and 50 vol.-% $H_2O$ | 102-104° C. | 5 minutes | pronounced (erosion) |
| 7 | Mixture of 50 vol.-% HF and 50 vol.-% $H_2O$ | 102-104° C. | 10 minutes | non-pronounced |
| 8 (comparative) | No etching (erosion only) | — | — | pronounced (erosion) |
| 9 (comparative) | No etching (sandblasted only) | — | — | pronounced (sandblasted) |
| 10 | Concentrated HF | 102-104° C. | 5 minutes | non-pronounced |
| 11 | Concentrated HF | 102-104° C. | 5 minutes | pronounced (sandblasted) |

Figure 3A:
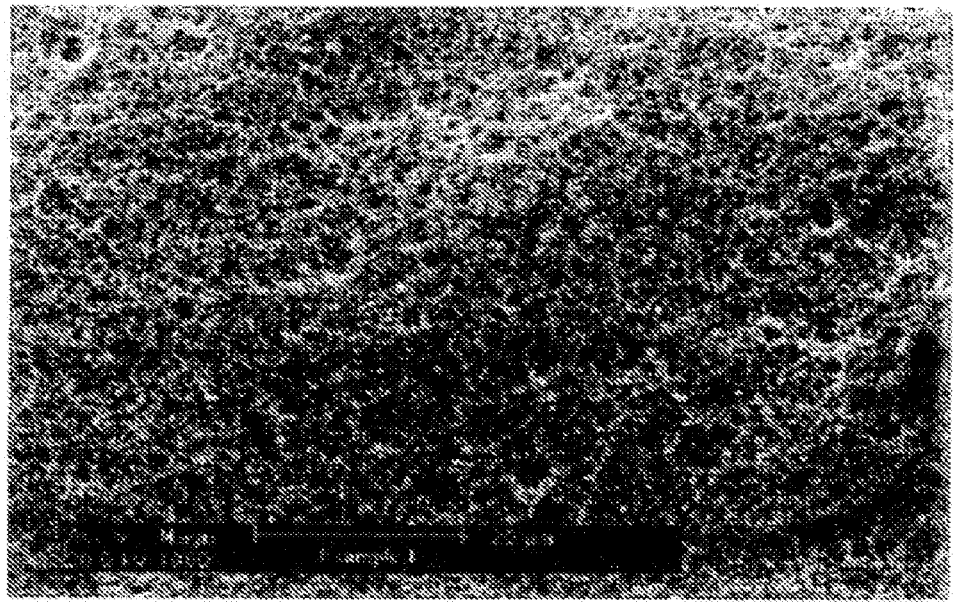
FIGS. 3A-3B are SEM pictures of the surface resulting from the treatment according to Example 1 in two different magnification levels, the scale given in the SEM picture corresponding to 20 μm (FIG. 3A) and 5 μm (FIG. 3B), respectively.
Figure 3B:
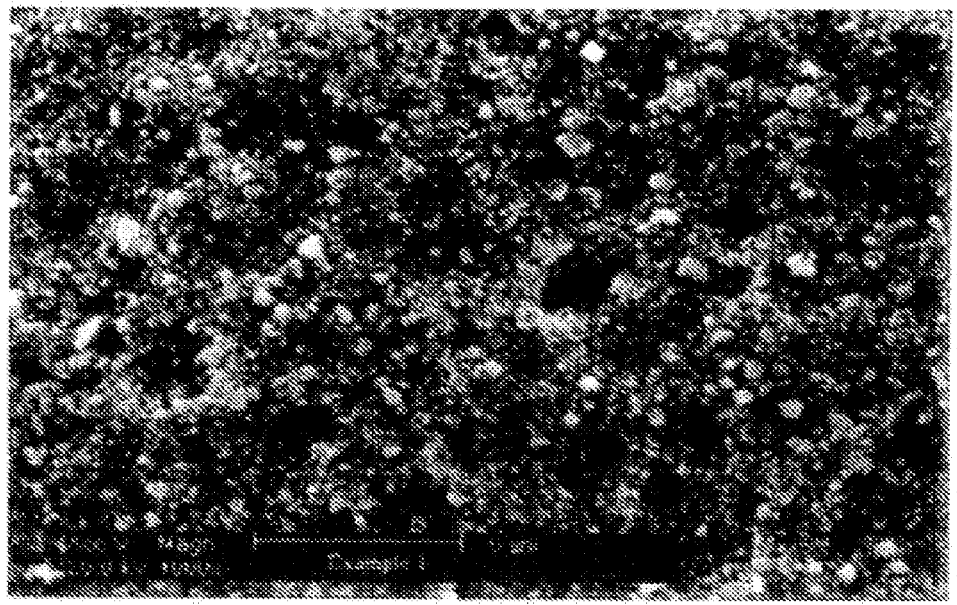
Figure 4A:
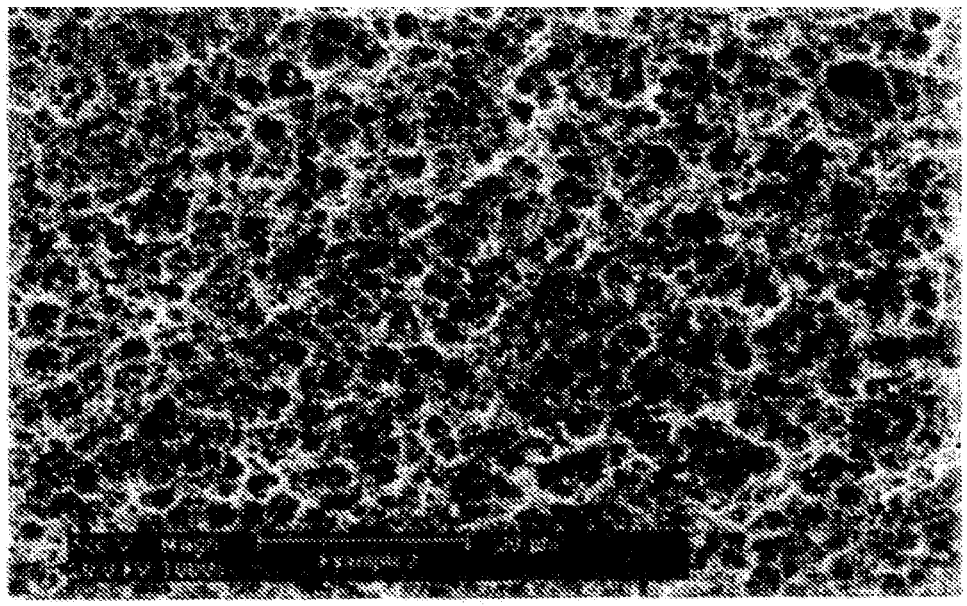
FIGS. 4A-4B are SEM pictures of the surface resulting from the treatment according to Example 2 in two different magnification levels, the scale given in the SEM picture corresponding to 20 μm (FIG. 4A) and 5 μm (FIG. 4B), respectively.
Figure 4B:
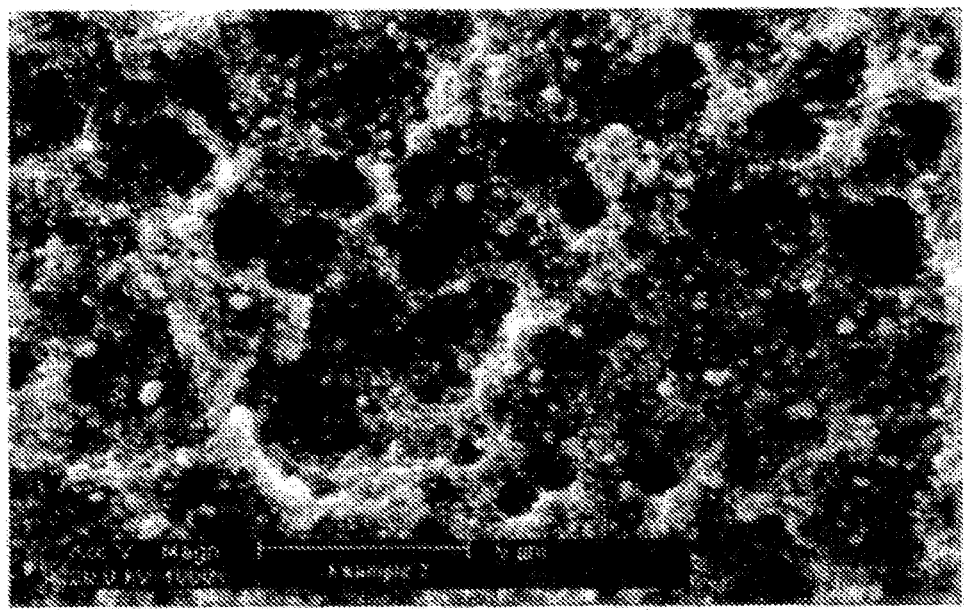
Figure 5A:
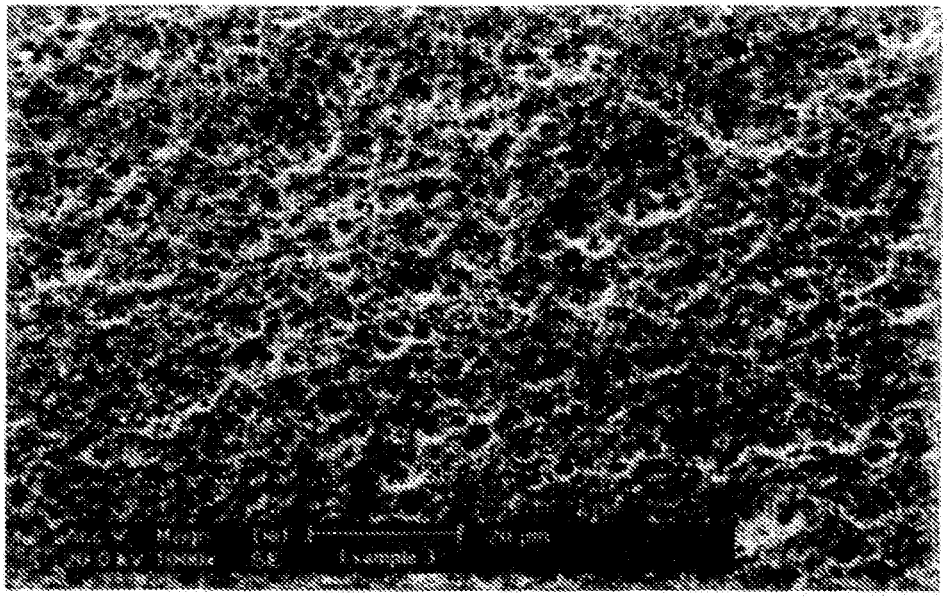
FIGS. 5A-5B are SEM pictures of the surface resulting from the treatment according to Example 3 in two different magnification levels, the scale given in the SEM picture corresponding to 20 μm (FIG. 5A) and 5 μm (FIG. 5B) respectively.
Figure 5B:
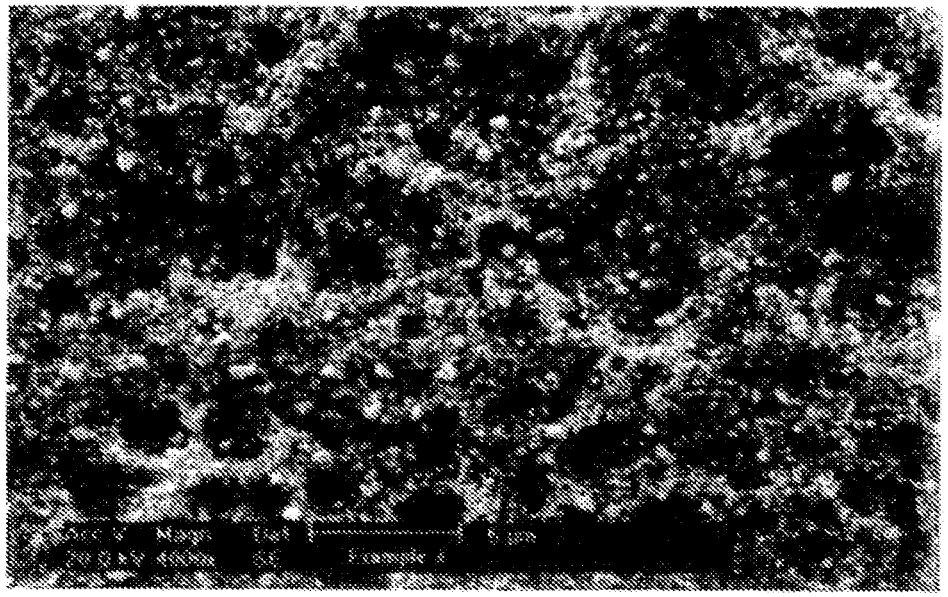
Figure 6A:
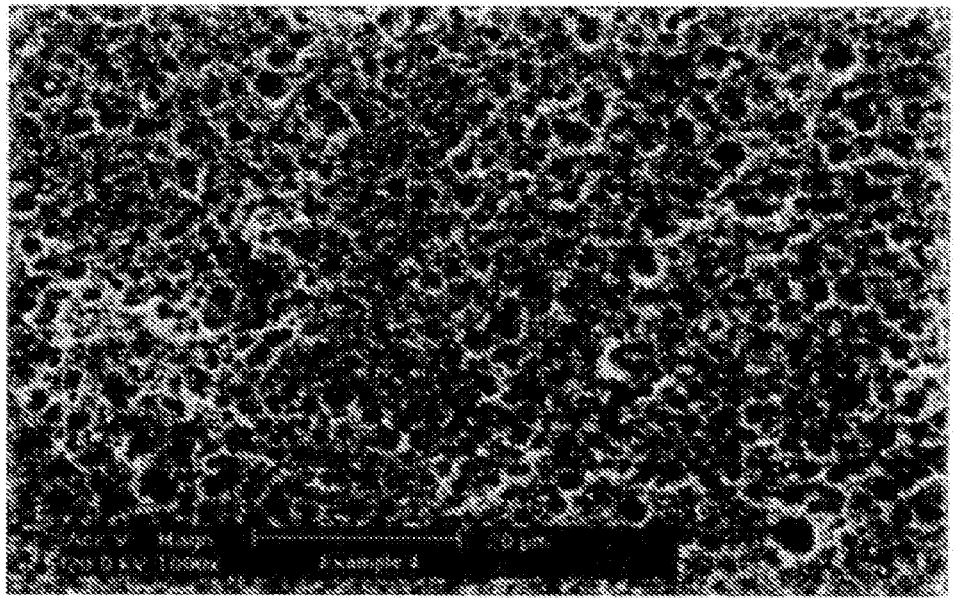
FIGS. 6A-6B are SEM pictures of the surface resulting from the treatment according to Example 4 in two different magnification levels, the scale given in the SEM picture corresponding to 20 μm (FIG. 6A) and 5 μm (FIG. 6B), respectively.
Figure 6B:
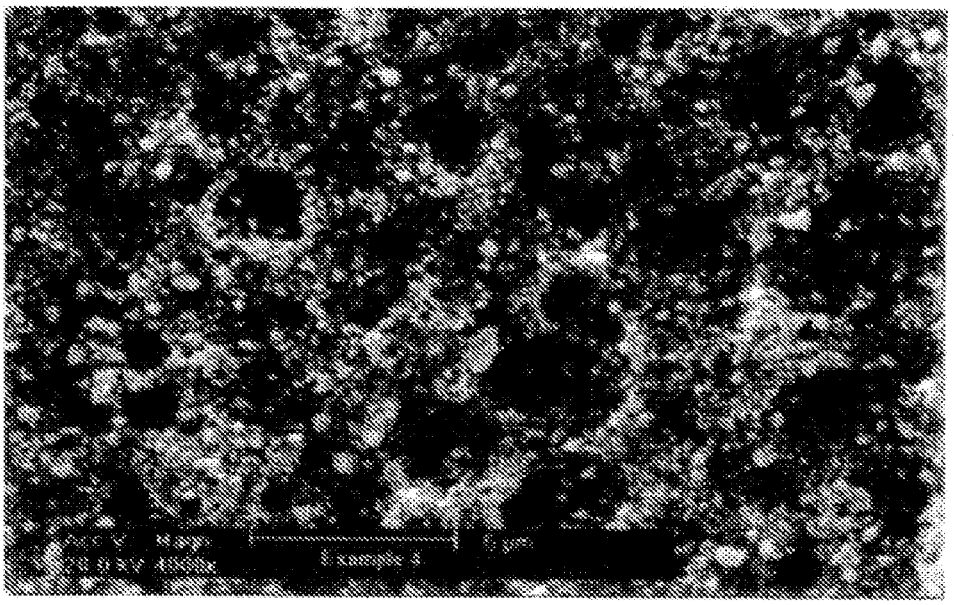
Figure 7A:
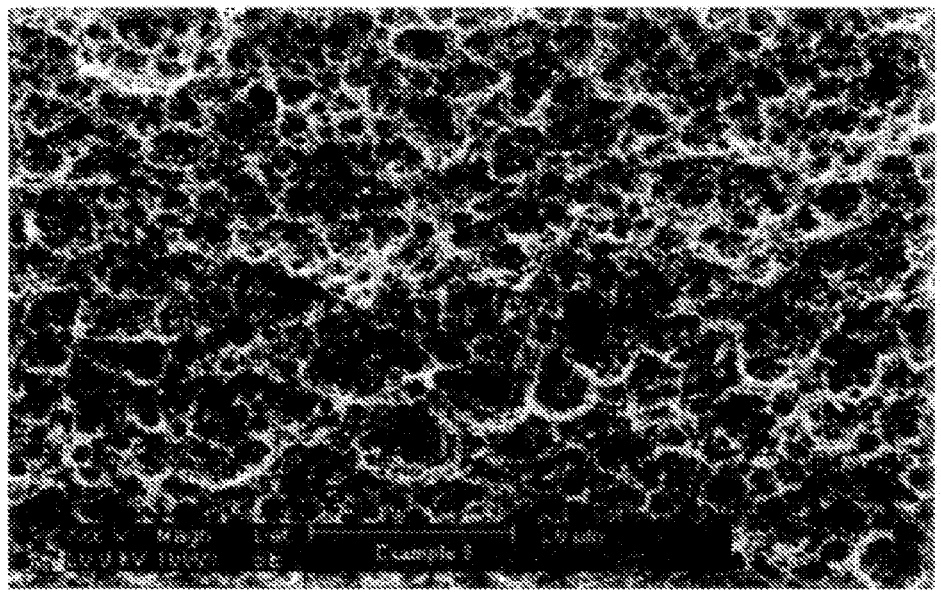
FIGS. 7A-7B are SEM pictures of the surface resulting from the treatment according to Example 5 in two different magnification levels, the scale given in the SEM picture corresponding to 20 μm (FIG. 7A) and 5 μm (FIG. 7B), respectively.
Figure 7B:
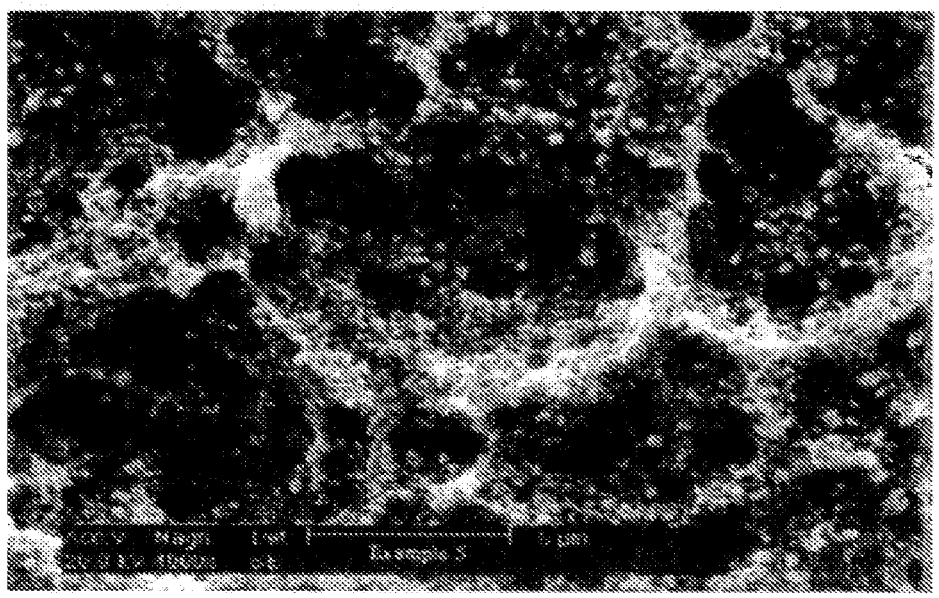
Figure 8A:
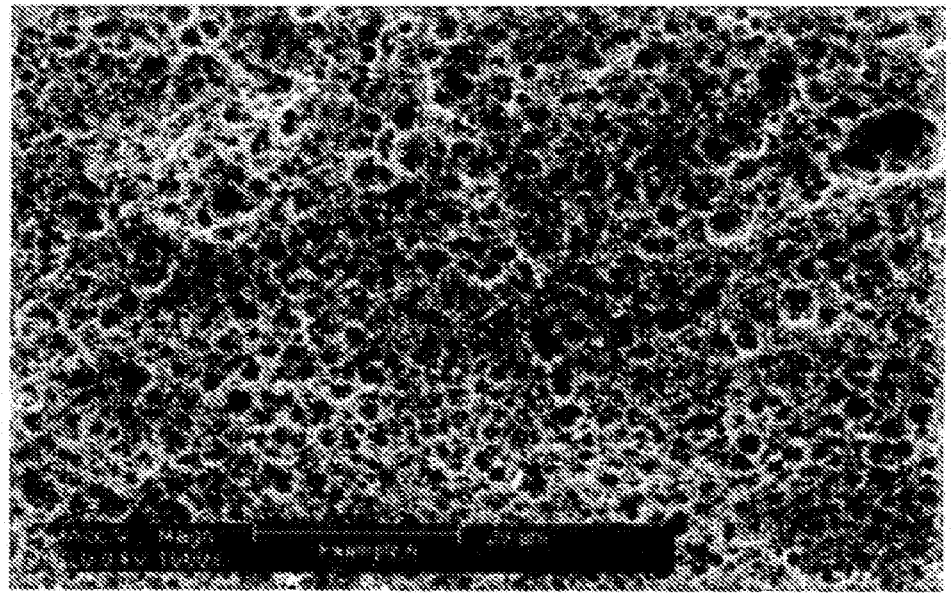
FIGS. 8A-8B are SEM pictures of the surface resulting from the treatment according to Example 6 in two different magnification levels, the scale given in the SEM picture corresponding to 20 μm (FIG. 8A) and 5 μm (FIG. 8B), respectively.
Figure 8B:
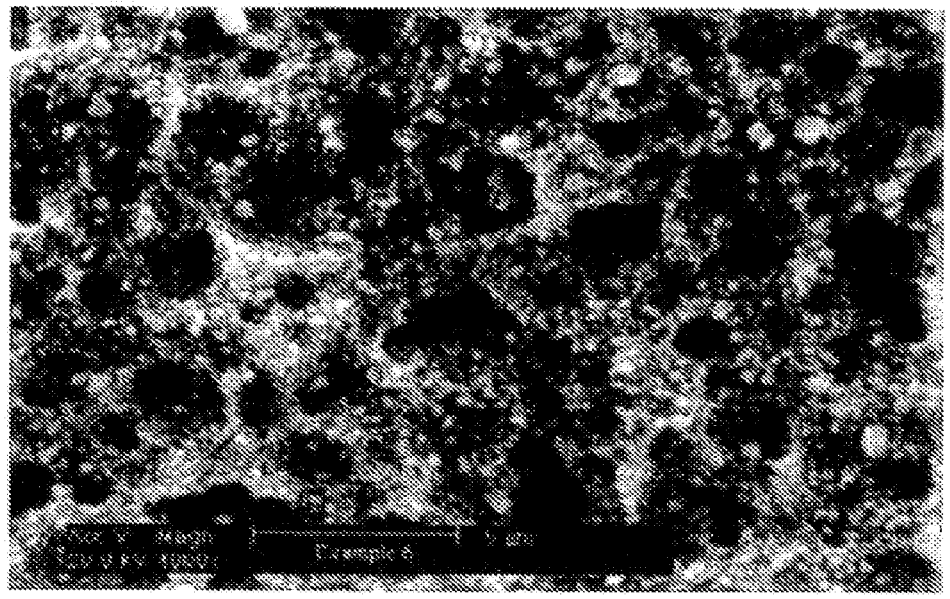
Figure 9A:
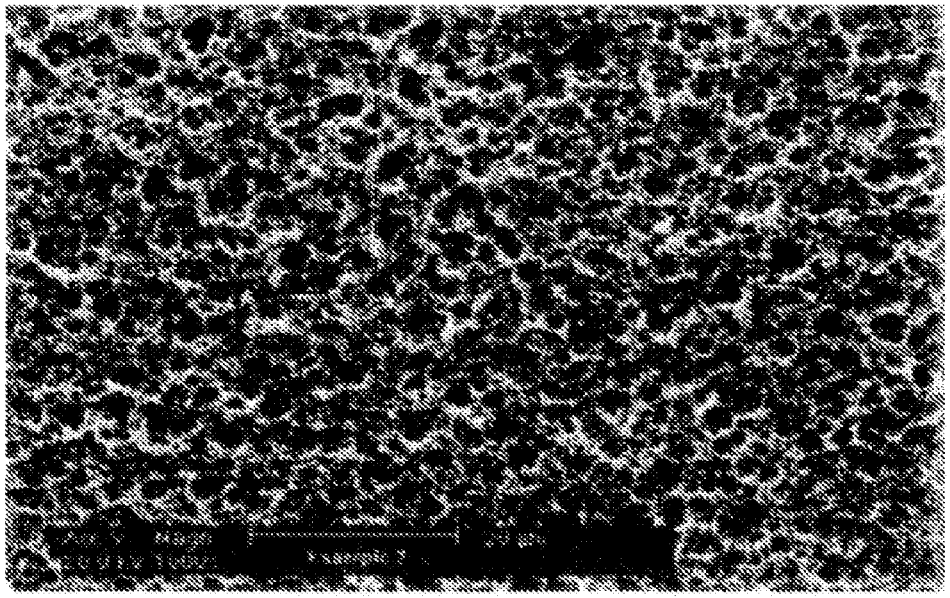
FIGS. 9A-9B are SEM pictures of the surface resulting from the treatment according to Example 7 in two different magnification levels, the scale given in the SEM picture corresponding to 20 μm (FIG. 9A) and 5 μm (FIG. 9B), respectively.
Figure 9B:
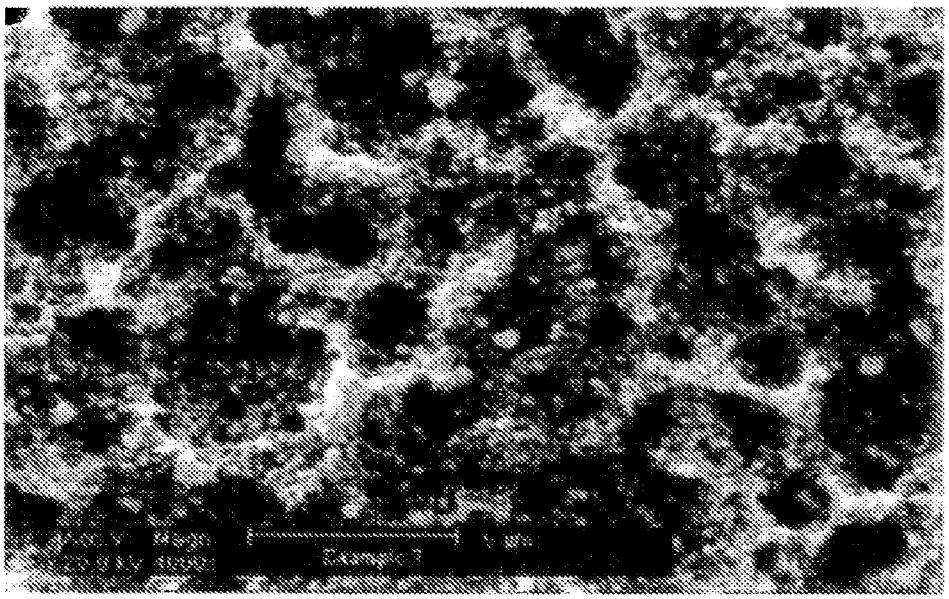
Figure 10A:
FIGS. 10A-10B are SEM pictures of the surface according to Example 8 in two different magnification levels, the scale given in the SEM picture corresponding to 50 μm (FIG. 10A) and 20 μm (FIG. 10B), respectively.
Figure 10B:
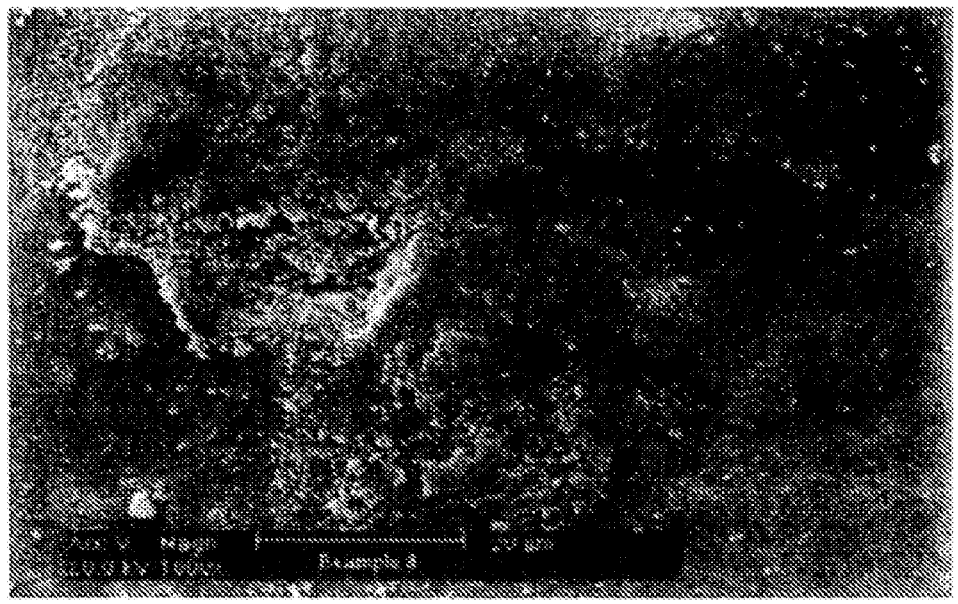
Figure 11A:
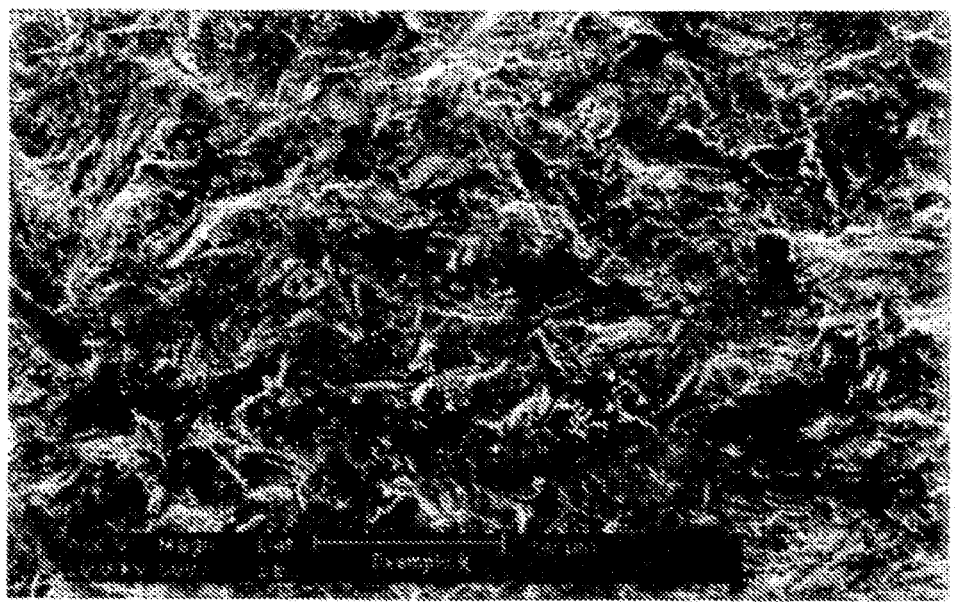
FIGS. 11A-11B are SEM pictures of the surface according to Example 9 in two different magnification levels, the scale given in the SEM picture corresponding to 50 μm (FIG. 11A) and 20 μm (FIG. 11B), respectively.
Figure 11B:

For Examples 1 to 9, the surface structure obtained by the above treatment is shown in FIGS. 3 to 11 of which FIG. 3 is an SEM picture of the surface resulting from the treatment according to Example 1 in two different magnification levels, the scale given in the SEM picture corresponding to 20 μm (above) and 5 μm (below), respectively;

FIG. 4 is an SEM picture of the surface resulting from the treatment according to Example 2 in two different magnification levels, the scale given in the SEM picture corresponding to 20 μm (above) and 5 μm (below), respectively;

FIG. 5 is an SEM picture of the surface resulting from the is treatment according to Example 3 in two different magnification levels, the scale given in the SEM picture corresponding to 20 μm (above) and 5 μm (below), respectively;

FIG. 6 is an SEM picture of the surface resulting from the treatment according to Example 4 in two different magnification levels, the scale given in the SEM picture corresponding to 20 μm (above) and 5 μm (below), respectively;

FIG. 7 is an SEM picture of the surface resulting from the treatment according to Example 5 in two different magnification levels, the scale given in the SEM picture corresponding to 20 μm (above) and 5 μm (below), respectively;

FIG. 8 is an SEM picture of the surface resulting from the treatment according to Example 6 in two different magnification levels, the scale given in the SEM picture corresponding to 20 μm (above) and 5 μm (below), respectively;

FIG. 9 is an SEM picture of the surface resulting from the treatment according to Example 7 in two different magnification levels, the scale given in the SEM picture corresponding to 20 μm (above) and 5 μm (below), respectively;

FIG. 10 is an SEM picture of the surface according to Example 8 in two different magnification levels, the scale given in the SEM picture corresponding to 50 μm (above) and 20 μm (below), respectively; and FIG. 11 is an SEM picture of the surface according to Example 9 in two different magnification levels, the scale given in the SEM picture corresponding to 50 μm (above) and 20 μm (below), respectively.

As can be seen from FIGS. 3 to 9, etching according to the present invention of a surface made of an yttria-stabilized zirconia ceramic leads to a surface having crater-like structures. This surface is highly osteointegrative.

Figure 12:
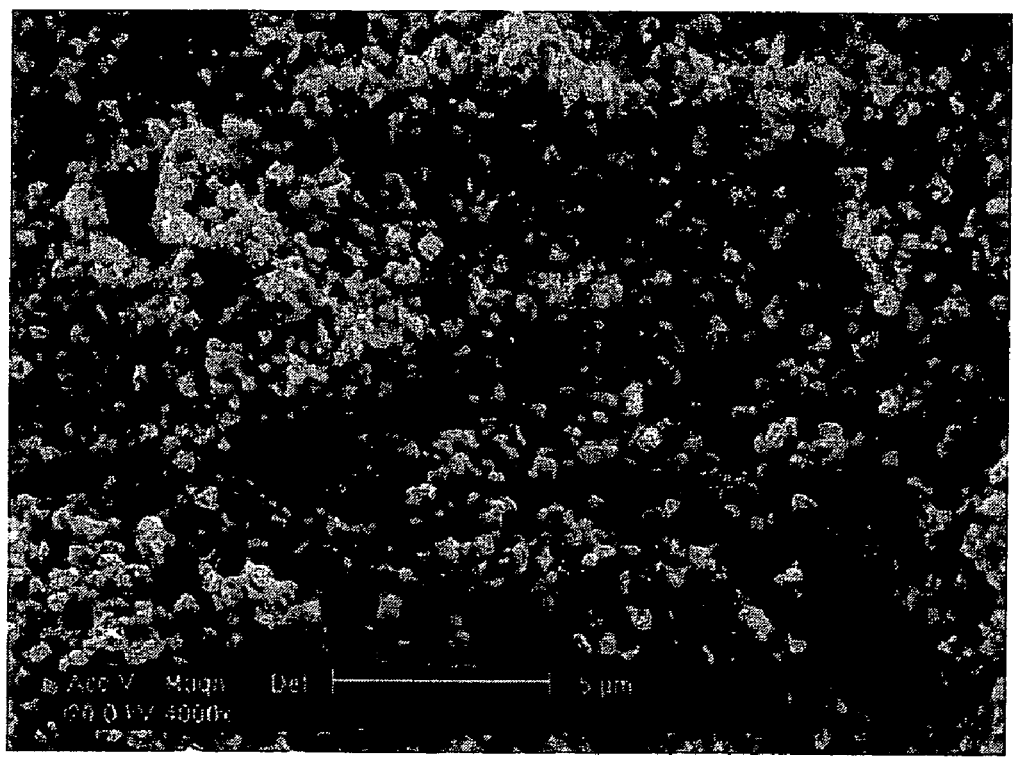
FIG. 12 is an SEM picture of the surface obtained in a further example, the scale given in the SEM picture corresponding to 5 μm.

Similar structures are obtained by etching other yttria-stabilized zirconia ceramics. In a further example, a disc made of $ZrO_2$-TZP/TZP-A Bio-HIP® ($ZrO_2$) Bioceramic available from Metoxit AG, Switzerland, is etched with a mixture of 50 vol.-% concentrated hydrofluoric acid (HF) and 50 vol.-% of concentrated phosphoric acid as etching solution, the etching time being from about 20 to about 60 seconds and the etching temperature being about 106° C. An SEM picture of the surface obtained is given in FIG. 12, the scale given in the SEM picture corresponding to 5 μm.

2. Parameters Characterizing the Surface Topography

For Examples 1 to 11, the topography of the surface is quantitatively examined using a confocal 3D white light microscope (μSurf, NanoFocus AG, Oberhausen, Germany) over an area of 770 μm×770 μm to calculate the three-dimensional topography parameters $S_k$ and $S_{sk}$. The lateral resolution of the microscope is 1.5 μm (512×512 pixels).

The specific measurement parameters are as follows:

| | |
|---|---|
| Measuring range: | 770 μm × 770 μm |
| Aperture: | 50% |
| Illumination: | Maximal intensity Xe-Lamp |
| Objective: | 20x |
| Drive: | Piezo |
| Stepsize: | 0.6 μm |
| Algorithm: | mean/fast |

The ceramic samples are coated with a Au/Pd layer having a thickness of about 20 nm. To this end, a sputter coater (SCD 050; BAL-TEC AG, Liechtenstein) was used. The settings are as follows:
Coating distance: 50 mm
Evacuation: to $4\times10^{-1}$ mbar
Rinsing: with Argon
Current: 65 mA
Time: 55 s By these settings, an Au/Pd layer having a thickness of about 20 nm is obtained.

The 3D specific Skewness $S_{sk}$ and Core Roughness Depth $S_k$ are calculated using a Gaussian filter with a cut-off wavelength of 10 µm. The Gaussian filter used to analyze the Core Roughness Depth and its associated parameters is a specific filter described in ISO 13 565 Part 1 (DIN 4776). The cut-off wavelength $\lambda_c$ is defined, according to DIN 4768, as the wavelength of the sinusoidal wave which is separated by the filter into 50% roughness and 50% waviness.

The calculation of the roughness parameter $S_k$ and $S_{sk}$ is carried out by the WinSAM software (University of Erlangen, Germany).

Details to the WinSAM software:
Windows Surface Analysis Module; Version 2.6, University of Erlangen, Germany; "Polynom 3. Grades, MA-Gauss-Filter 7 Punkte=cut-off (10×10 µm²); KFL-Analyse Amplitudendichte 10 nm".

The filter creates a separation into waviness and roughness.

This derivation and therefore also the determined value for the roughness parameter is dependent on the selected cut-off wavelength $\lambda_c$. For determining the $S_k$ and $S_{sk}$ values, the cut-off wavelength $\lambda_c$ is set to 10 µm as given above.

Figure 13:
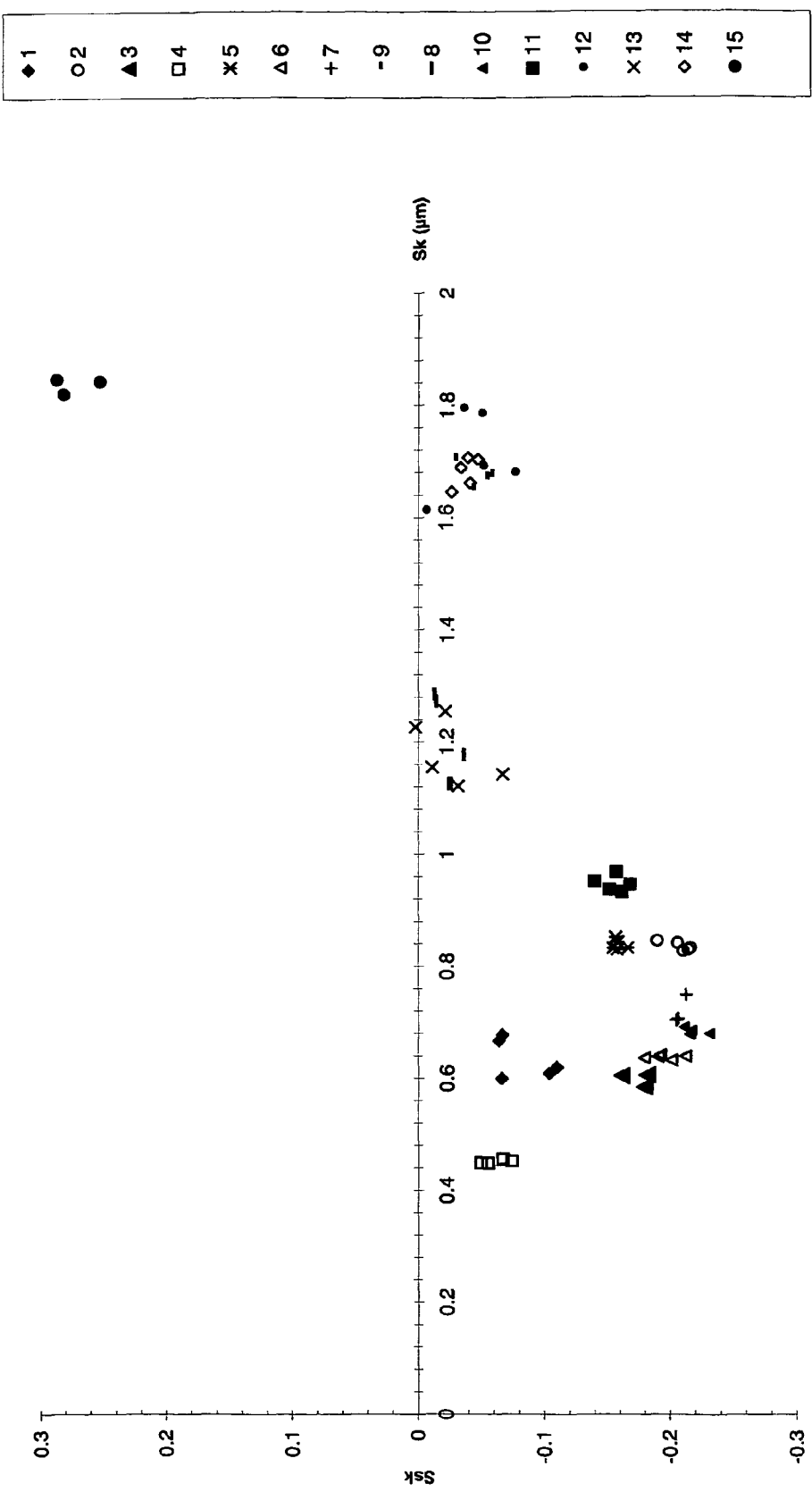
FIG. 13 is a diagram of the results in which the $S_{sk}$ values and the $S_k$ values of Examples 1 to 11 are represented pointwise.

The results are given in the diagram of FIG. 13 in which the $S_{sk}$ values and the $S_k$ values of Examples 1 to 11 are represented pointwise.

Comparatively, the $S_k$ and $S_{sk}$ values of the commercially available implants Z-Zit® (Example 12) of Ziterion GmbH, Germany, Z-Lock® (Example 13) of Z-Systems AG, Germany, White Sky® (Example 14) of Bredent medical GmbH, Germany, and Ti-SLActive® (Example 15) of Straumann, Switzerland, have also been determined according to the method described above.

As can be seen from FIG. 13, the surface topography of Examples 1 to 7 and 10 to 11 obtained according to one process in accordance with the present invention has a Core Roughness Depth $S_k$ between about 0.4 µm and about 1 µm. In these Examples, the Skewness $S_{sk}$ is less than 0. FIG. 13 also clearly illustrates that the surface topography obtained according to the present invention is completely different from the surface topography of commercially available implants, in particular SLActive® (available from Straumann Holding AG, Basel CH), which have a Core Roughness Depth $S_k$ significantly higher than 1 µm.

3. In vitro Cell Tests

In vitro cell tests are carried out using the human osteosarcoma cell line MG-63 because of its ability to differentiate into mature osteoblasts.

The cell line is cultured in a mixture of Dulbecco's modified Eagles's Medium (DMEM; available from Sigma, Switzerland), Penicillin-Streptomycin Solution (100X; available from Sigma, Switzerland) and FBS.

On each of the discs according to Examples 1, 2, 7, 9 and 15, approximately 9000 cells are plated.

After culturing each of the respective discs in a medium containing vitamin D3, they are removed and washed with 1 ml PBS (RT). 350 µl of RLT-buffer (plus β-mercaptoethanol) is added to each disc and incubated for 2 to 3 minutes.

The RLT buffer is removed by simultaneously scratching with a pipette tip over the surface of the discs (to remove all cells) and frozen at −25° C. until RNA extraction.

RNA is isolated using the QIAGEN—Kit RNeasy Micro Kit®. Then, cDNA is produced and the expression of osteocalcin, osteonectin and TGFbeta, which are known to be involved in the bone formation process, is analysed by "Real time PCR". As reference gene, 18S rRNA is used. Osteocalcin, osteonectin and TGFbeta are known to be suitable biochemical markers for the bone formation process.

For the calculation of the relative fold expression of the respective marker, the Livak method or $2^{-\Delta\Delta Ct}$ method is used.

This method is based on the assumption that target and reference genes are amplified with efficiencies close to 100% (corresponding to an amplification rate of 2). The Livak method puts the $E_{(target)}=E_{(reference)}=2$, wherein E is the efficiency of the reaction.

The threshold cycle (Ct) of the target gene is normalized to the reference gene for the test sample and the calibrator sample. As a reference gene, 18S tRNA is used, and as a calibrator sample, cells cultured on the disc of Example 9 is used.

The ΔCt of the test sample is defined as follows:

$$\Delta Ct_{(test\ sample)} = Ct_{(test\ sample)} - Ct_{(reference\ gene)}$$

wherein the ΔCt of the calibrator is defined as follows:

$$\Delta Ct_{(calibrator)} = Ct_{(test\ calibrator)} - Ct_{(reference\ calibrator)}$$

The ΔCt of the test sample is normalized to the ΔCt of the calibrator, resulting in the ΔΔCt:

$$\Delta\Delta Ct = \Delta Ct_{(test\ sample)} - \Delta Ct_{(calibrator)}$$

and the normalized expression ratio was calculated by the following formula:

$$\text{Normalized expression ratio} = 2^{-\Delta\Delta Ct}$$

Figure 14:
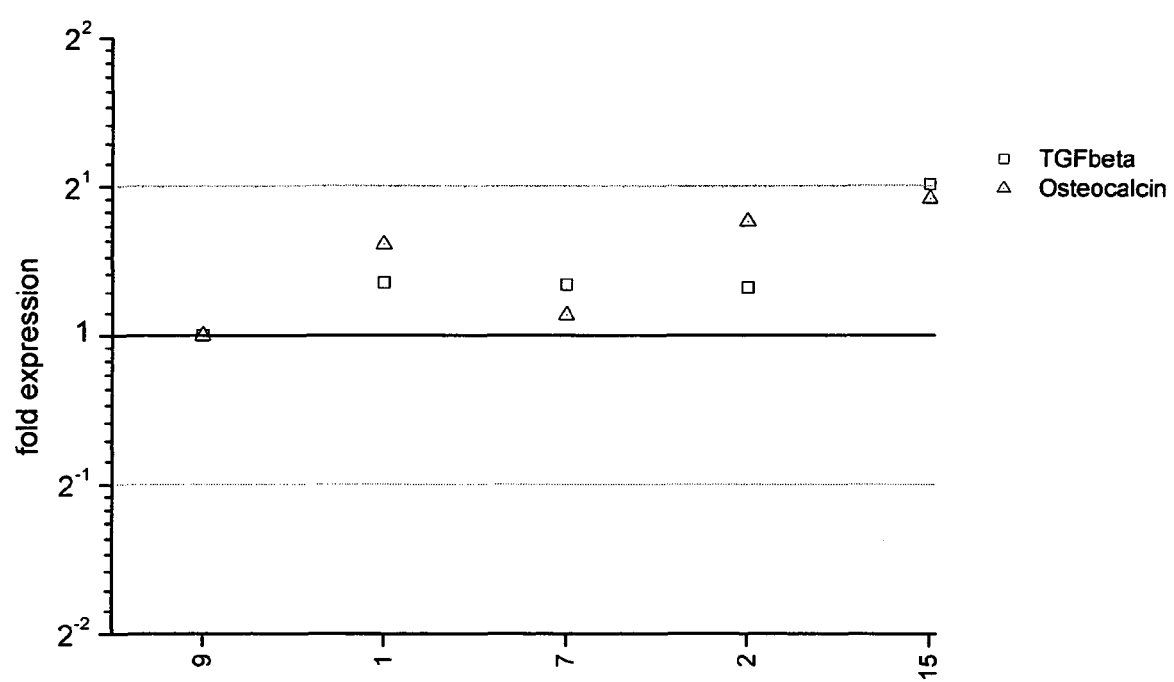
FIG. 14 shows the fold expressions of osteocalcin and TGFbeta on Examples 1, 2, 7 and 15 relative to Example 9.

The fold expressions of osteocalcin and TGFbeta on Examples 1, 2, 7 and 15 relative to Example 9 are shown in FIG. 14. As can be seen from FIG. 14, all examples treated according to the present invention exhibit a higher expression of osteocalcin and TGFbeta than comparative Example 9. This substantiates the finding that the examples treated according to the present invention have improved osteointegrative properties. A higher expression of osteocalcin and TGFbeta is also found for Example 15 relating to Ti-SLActive® which is well known for its high osteointegrative properties.

Figure 15:
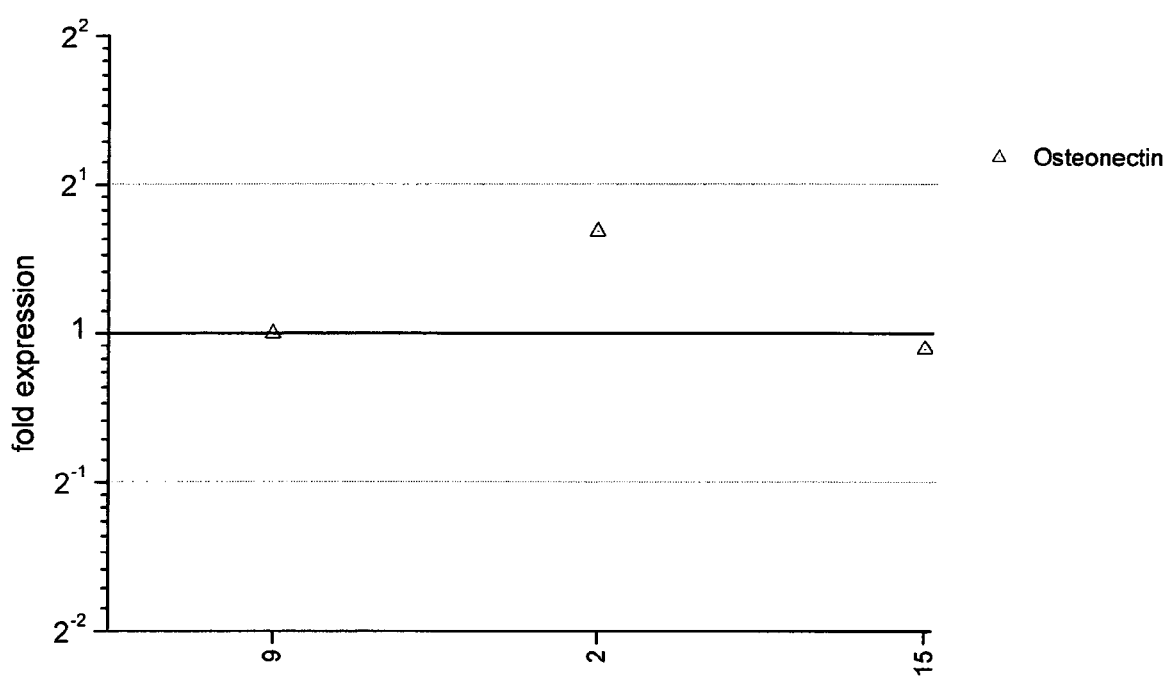
FIG. 15 shows an expression of osteonectin (from Example 2) superior over both comparative Example 9 and Example 15 (Ti-SLActive®).

Example 2 has further been analysed for its expression of osteonectin. As shown in FIG. 15, Example 2 shows an expression of osteonectin superior over both comparative Example 9 and Example 15 (Ti-SLActive®).

The invention claimed is:

1. Dental implant having a bone tissue contacting region having a surface made of a ceramic material, wherein the surface has an osteointegrative topography defined by a Core Roughness Depth $S_k$ of less than 1 µm, and the skewness $S_{sk}$ of the topography being less than 0 as determined by the following equation:
$S_{sk} = -m * S_k$ wherein m ranges from greater than 0 to 1.

2. Dental implant according to claim 1, the Core Roughness Depth $S_k$ being between 0.4 µm and 1 µm.

3. Dental implant according to claim 1, the ceramic material having an average grain size from 0.1 µm to 0.6 µm.

4. Dental implant according to claim 1, the ceramic material being based on zirconia.

5. Dental implant according to claim 1, the ceramic material being yttria-stabilized zirconia.

6. Dental implant according to claim 5, the composition of the yttria-stabilized zirconia comprising 4.5 to 5.5 weight-% of $Y_2O_3$ and less than 5 weight-% of $HfO_2$, the total amount of $ZrO_2$, $Y_2O_3$ and $HfO_2$ being more than 99 weight-%.

7. Dental implant according to claim 1, the dental implant being a one-part dental implant.

8. Dental implant according to claim 1, the dental implant being a two-part dental implant.

9. Dental implant according to claim 8, wherein the two-part dental implant has an anchoring part with the bone tissue contacting region and a mounting part for receiving a prosthetic build-up construction.

10. Dental implant according to claim 9, the bone tissue contacting region having a threaded section.

11. Dental implant according to claim 10, the threaded section having the osteointegrative topography.

12. Dental implant according to claim 1, the ceramic material being yttria-stablized zirconia having an average grain size from 0.1 μm to 0.6 μm.

13. Dental implant according to claim 1, wherein the ceramic material comprises one or more of zirconia, alumina, silica, and mixtures thereof.

14. Dental implant according to claim 1, wherein the surface has a macroscopic roughness provided by one or more of sandblasting, milling and injection molding in a mold with cavities to impart the macroscopic roughness.

15. Dental implant according to claim 14, wherein the surface has a microstructure provided by etching the surface.

16. Dental implant according to claim 1, wherein the dental implant has a soft tissue contacting region also having the surface topography.

17. Dental implant according to claim 1, wherein the whole implant surface is made of a ceramic material, at least a portion of the surface having the osteointegrative topography.

18. Dental implant according to claim 1, wherein the dental implant is made fully of a ceramic material.

19. Dental implant according to claim 1, wherein the dental implant has a core made of a metal or another ceramic material.

* * * * *

UNITED STATES PATENT AND TRADEMARK OFFICE
CERTIFICATE OF CORRECTION

PATENT NO. : 8,408,906 B2
APPLICATION NO. : 12/105700
DATED : April 2, 2013
INVENTOR(S) : de Wild et al.

It is certified that error appears in the above-identified patent and that said Letters Patent is hereby corrected as shown below:

In the Claims

At col. 12, line 61 (claim 1) "=" should be -- $\leq$ --

Signed and Sealed this
Eighteenth Day of June, 2013

Teresa Stanek Rea
*Acting Director of the United States Patent and Trademark Office*